US008121863B2

(12) United States Patent
Diakides et al.

(10) Patent No.: US 8,121,863 B2
(45) Date of Patent: Feb. 21, 2012

(54) METHOD FOR DETECTING ABNORMALITIES IN MEDICAL SCREENING

(76) Inventors: Nicholas A. Diakides, Falls Church, VA (US); Mary Diakides, Falls Church, VA (US)

( * ) Notice: Subject to any disclaimer, the term of this patent is extended or adjusted under 35 U.S.C. 154(b) by 1770 days.

(21) Appl. No.: 11/222,947

(22) Filed: Sep. 12, 2005

(65) Prior Publication Data
US 2007/0058845 A1    Mar. 15, 2007

(51) Int. Cl.
*G06Q 10/00* (2006.01)
(52) U.S. Cl. ............................................... 705/3; 705/2
(58) Field of Classification Search .................. 705/2–4; 600/300
See application file for complete search history.

(56) References Cited

U.S. PATENT DOCUMENTS

| 5,384,643 A * | 1/1995 | Inga et al. ...................... 358/403 |
| 7,200,612 B2 * | 4/2007 | Brady et al. ................ 707/104.1 |
| 2004/0102689 A1 * | 5/2004 | Metz et al. ..................... 600/407 |
| 2005/0075544 A1 * | 4/2005 | Shapiro et al. ................ 600/300 |

* cited by examiner

*Primary Examiner* — Vivek D Koppikar
*Assistant Examiner* — Rajiv Raj

(57) ABSTRACT

A computer-aided detection process for interpreting body images using knowledge based SMART algorithms. The process interprets, in real time, body scan images submitted from screening centers and other certified medical practitioners around the world, and then renders an accurate, reliable and reproducible analysis of each patient's health status relative to the specific body image submitted and returns the results to the originating source.

4 Claims, 1 Drawing Sheet

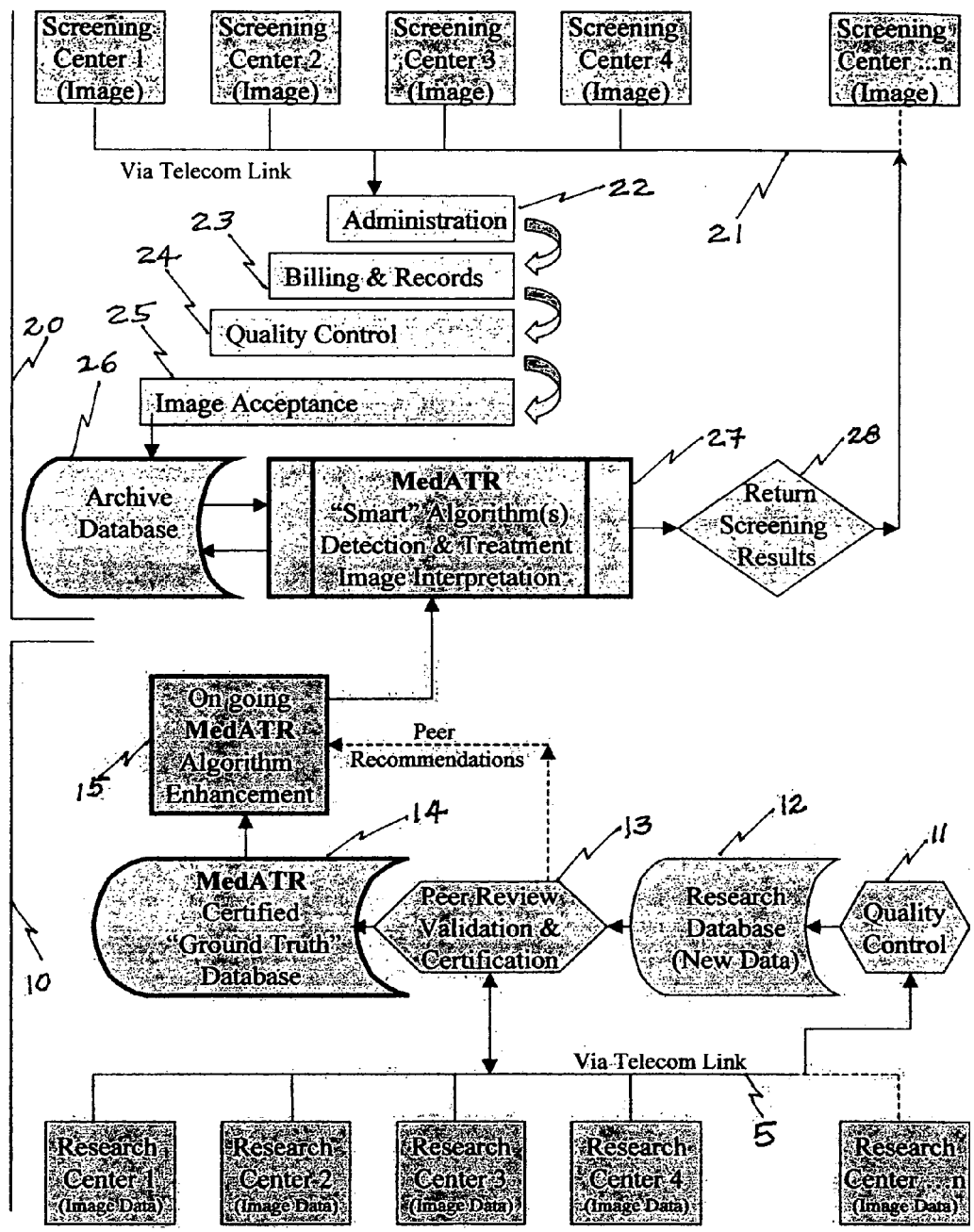

METHOD FOR DETECTING ABNORMALITIES IN MEDICAL SCREENING

REFERENCE TO RELATED APPLICATIONS (Not Applicable)

FEDERALLY SPONSORED RESEARCH (Not Applicable)

REFERENCE TO MICROFICHE APPENDIX (Not Applicable)

BACKGROUND OF THE INVENTION

1. Field of the Invention

This invention relates to a method for detecting abnormalities in medical screenings and, more specifically, to a method for comparing an image obtained during a body scan to stored images in a medical imaging database, whereby abnormalities in the image will be automatically determined by using an iterative algorithm.

2. Description of Related Art

The military establishment has developed an Automated Target Recognition (ATR) technology using thermal imaging and advanced image processing, with an iterative ATR algorithm designed solely for military recognition of targets of regular and known shape and size. Military targets, such as tanks, weapons, wheels, gun barrels, etc., have unique characteristics, and can be easily provided as a database for comparing military target acquisition in real time. These ATR algorithms are designed solely for military target recognition and are simply not suitable for the detection of medical abnormalities, nor is there currently a database of medical abnormalities, with well defined signature features available, which would be conducive to the design of an iterative algorithm.

At the present time, readings of images from body scans depend on the subjective interpretation, abilities and experience of the examining physician, and hence make their reproduction by others extremely difficult. In the case of medical infrared (IR) imaging, also known as thermography, signatures vary widely and lack consistent and regular geometric properties. Even where there are some signatures available, they generally have not been acquired by a standardized protocol and thus do not allow reproducibility of readings, but instead generate unreliable results. It is difficult to recognize targets of this type, for which a priori knowledge of features does not exist, and accordingly, identification and classification of the body abnormality represented by the signature is essentially impossible, which renders the generation of a reliable database essential.

SUMMARY OF THE INVENTION

The present invention addresses and resolves the concerns and problems above referenced by establishing a standardized, knowledge-based database of medical signatures collected from patients, and then quantifying the signatures into categories ranging from normal to diseased. These images must adhere to a strict clinical protocol, be certified through peer-review, and be validated by "ground truth" in qualified medical centers. The resulting images will then be used as a basis for developing an iterative algorithm for use in Computer-Aided Detection (CAD) of medical abnormalities, as well as for post monitoring of the treatment therapies.

BRIEF DESCRIPTION OF THE DRAWINGS

The single FIGURE is a flow diagram showing both the method of developing a SMART algorithm and a revenue process which is activated upon the receipt of an image to be interpreted.

DETAILED DESCRIPTION OF THE PREFERRED EMBODIMENT

This invention can best be understood by describing the method of detecting medical abnormalities in body scans by referring to a specific modality, and accordingly, the creation of an infrared (IR) database, from IR signatures, will be used as a basis for better understanding the process necessary to render this technique, for the early detection of medical abnormalities, a viable approach to better detection, diagnosis and treatment of health problems. Modalities other that IR, which can be just as readily adaptable to this program, include mammography, x-ray, ultrasound, MRI, PET, etc. The same process, as described in terms of an IR database, will apply for the creation of a database for any single or combined multi-modal dataset assembly, however, the protocol will be customized to suit the specific modality.

The use of IR is based on understanding angiogenesis, which is the principle that chemical and blood vessel activity in both pre-cancerous tissue and the area surrounding a developing breast cancer is almost always higher than in normal breast tissue. In an ever-increasing need for nutrients, cancerous tumors increase circulation to their cells by opening existing blood vessels and creating new ones. IR uses ultra-sensitive infrared cameras and sophisticated computers to detect, analyze, and produce high-resolution diagnostic images of these temperature variations. Because of IR's extreme sensitivity, these temperature variations may be among the earliest signs of breast cancer and/or a pre-cancerous state of the breast. Early detection is the most valuable procedure in the assessment of patient risk. Establishing one's personal IR database from the age of perhaps 18 to well into the senior years can make early detection 3 to 20 years before cancer reaches 3-5 mm. in size. The image interpretation process has been proven to be 90%+ or −5% accurate. IR is a non-invasive, early screening modality which can detect medical abnormalities by measuring minute changes in temperature, thus providing functional imaging of metabolic processes.

Looking now more specifically at the requirements for effecting this method of early detection and treatment of medical abnormalities and to lend credibility and a clearer understanding of just what the images portray, the focus will be on those image signatures generated by breast cancer. Before abnormalities can be identified, it is first necessary to establish a "knowledge-based" medical imaging database, also referred to as a "ground truth" database, which can be used as an "atlas" for the development of an iterative algorithm using the Simultaneous Multiplicative Algebraic Reconstruction Technique (SMART). To develop a "knowledge-based" medical IR imaging database, it is necessary to collect thermal images of the breast, develop, quantify and characterize a unique database of standardized IR signatures of the breast, and to define and compare the relative ability of different scales to quantify normal and malignant IR signatures. This database will then be used as an "atlas" or standardized database for developing a SMART algorithm. As new images become available, they function as an on-going enhancement to the algorithm as they are added to the database, where blocks of image data or ordered subsets are iteratively incorporated into the algorithm to accelerate the development, dependability and perfection of the SMART algorithm. This extensive database is developed by qualified, multi-modality research centers, as shown in the flow diagram. These research centers utilize the latest uncooled IR detector equipment for body scanning and provide extremely refined thermal image signatures which meet the protocol for the IR images. The research centers consist of clinics, universities, hospitals and other research facilities with capable sources, which in many instances, already have extensive databases which have gone largely unused. These databases can be reviewed to make sure they were derived with an appropriate protocol, allowing them to be used as a base for the initial comparison of newly obtained signatures and for refining the SMART algorithm.

Patient images are taken under the image protocol standards set for each modality and, under the IR protocol, they are read "blindly". A blind reading is an independent reading without knowledge of a patient's medical history or other diagnostic information. As shown in the flow diagram of the FIGURE, the image data is uploaded via a telecom link (5) to a processing and oversight center (10) where the image data is processed at step (11) of the flow diagram for quality control. Validated data is then accumulated in step (12), where it is stored in a temporary database until all quality control tests are completed. The valid data is then statistically certified in step (13) and simultaneously sent for storage to a permanent "ground truth" database in step (14), as well as being processed in step (15) to initiate the acceptance of the updated "ground truth" database from step (14), which enhances the iterative algorithm in step (15).

The research centers are independent, but all must adhere to prescribed image protocols, meet certain criteria to assure that a predetermined procedure for imaging a patient is consistent throughout all the centers, and assure that participants in the project meet a blind test correlation standard. For instance, during the IR scans the room temperature must be maintained between 18-20 degrees centigrade, the patient must have at least a 3-5 minute cooling down period prior to the scan, and at least three images should be generated: an anterior and two lateral views, with a fourth image from the under-surface optional.

In the processing and oversight center, shown as block (10) of the flow diagram, the images are either accepted or rejected during the analysis of the input images from the research centers and the oversight center follows up on rejected images, acceptance protocols are reviewed and the quality control protocol is adjusted as necessary. The rejected images are stored and the reason for document rejection is recorded. The research database (12) also accepts multi-modality readings, known as pathology and medical history and stores them separately for "ground truth" validation for peer review. All uploading and downloading is performed electronically to the database, where the images and results of the readings are stored. Under the IR protocol, three to four images, in different views, are taken for each patient and entered both in radiometric and JPEG form. Thereafter, one or more peer-certification readings are performed as specified by protocol, on every patient, by the research centers, which can download the relevant data for this purpose and subsequently upload their "blind" and multi-modality reading results to the database.

When this procedure is totally completed, the readings of the research centers are cross-correlated, as is the pathology for validation. In this manner it will be possible to confidently quantify and classify these images into categories. For the breast IR research dataset case there are three categories, namely: "normal", "equivocal", or "abnormal". Each of these will have unique signature characteristics that will be used as a basis to design "knowledge-based SMART algorithms. These algorithms screen images and provide SMART CAD for assisting physicians and health care personnel in early detection of medical abnormalities.

This database will be expanded continuously to include more patient images, thus allowing the periodic refinement of the algorithm. This will enable further algorithm enhancement leading to even higher performance. This method lends itself ideally to first-line screening where high-risk patients can be identified at a very early stage.

Once the database is established and the SMART algorithm has been developed and refined, then the service will be made available to subscribers for a nominal charge. As shown in the uppermost portion of the flow diagram, the flowchart shows a multitude of screening centers which represent image input centers for the general practitioners, physicians and hospitals who subscribe to the service. The screening centers must meet the same protocol requirements and follow the same patient and environment preparations as established for the research centers. This technique provides the physician with real-time, accurate and reliable interpretations of patients' Infrared Images of the breast for the early detection of cancer. The processing center (20) and the oversight center (10) of the flow diagram are, in reality, a business center and are part of the same center, but for ease of describing the functions attributed to processing the images derived from the research centers for refining the SMART algorithm and the functions associated with processing and screening the images submitted by the physicians, it is deemed more expedient to concentrate on each aspect of the process individually. The business center is not the screening center, nor is it an Infrared camera manufacturer, however it is an essential partner to all IR camera manufacturers and screening centers, by providing "ground truth analysis", which is a reliable and accurate interpretation of a patient's infrared images.

Perhaps it would be wise to explain just how this method for the early detection of medical abnormalities is anticipated to be the crux of an online service to provide physicians with real-time, accurate and reliable interpretations of a patient's image of a medical abnormality. Again, IR imaging of a breast abnormality is deemed to be the easiest way to describe the application of the instant technique to the actual processing and interpretation of images of medical abnormalities, but any of the other modalities are equally applicable.

Looking again at the flow diagram, the screening centers 1–$n$ are representative of the physicians, hospitals and other medical screening centers throughout the world, which provide patient IR images through a telecom link (21) to be analyzed for abnormalities by the SMART algorithm at step (27). The operational center (20) is effectively organized as an on-line pay-for-fee service to clients and specialists for the early detection of breast abnormalities while also identifying high risk patients. Images may also be stored in the archive database (26) for future reference, if the service is desired, to determine the efficacy of various pre/post treatment therapies. As the images are downloaded from the data link (21) they are automatically processed through administration (22), billing and records (23), quality control (24) and image acceptance (25). In the administration phase (22) the image is keyed for control and future reference upon being stored in the archive database (26) and a determination of the specific screening center and source of the image is established along with the modality and any information necessary to properly identify the image as belonging to a specific patient while securing the actual identity of the patient. In billing and records (23) a determination is made of what type and how many images have been received from the identified screening center and the center is so charged for the type of service requested and automatically billed. Before the images can be properly processed, they must pass a quality control (24) test to ensure that they subscribe to a predetermined level of specificity after which the image acceptance phase (25) assures that the images subscribe to the proper protocol in order to be acceptable and compatible with the archive database (26). The image is then stored in the archive database (26) while simultaneously being analyzed by the SMART algorithm to interpret the image for any existent abnormalities. The screening algorithm will analyze the results as: "Normal", "Equivocal" (needs more testing) or "Abnormal" (a definite medical problem) and return the results to the screening center/physician/diagnostician in real time. This entire procedure should take no more than five minutes and the charge for the service should fall within the range of one hundred to one hundred and fifty dollars.

The invention claimed is:

1. A method for detecting medical abnormalities, including the steps of:
   a) medically screening a patient in a medical screening center to obtain an image of a suspected medical abnormality;
   b) electronically transmitting the resultant image to a processing center;
   c) attaching an identification code to the image for maintaining the security of the image, the location of the user and for retrieving the image for future comparative analysis, if necessary;
   d) evaluating the image for quality control to assure that the image subscribes to a predetermined level of specificity;
   e) reviewing the image to assure that the image subscribes to the proper protocol;
   f) storing the image in an archive database for future reference, while simultaneously processing and analyzing the image for medical abnormalities by an iterative algorithm;
   g) electronically returning the screening results to the originator, with a determination and classification of abnormalities, if detected.

2. The method of detecting medical abnormalities as enumerated in claim 1, wherein the iterative algorithm of step (f) is developed by using a Simultaneous Multiplicative Algebraic Reconstruction Technique (SMART), which functions to continuously enhance the iterative algorithm as newly generated images, from a multiplicity of research centers, are accumulated in a "ground truth" database.

3. The method of detecting medical abnormalities as enumerated in claim 2, wherein the "ground truth" database is a unique database which is developed in accordance with the particular protocol utilized in the initial screening of a patient, the development of which includes the steps of:
   a) collecting refined image data conforming to a specific protocol, through various prequalified, multi-modal research centers;
   b) electronically forwarding the resultant images to a processing center;
   c) processing the image data for quality control purposes;
   d) statistically certifying the image data as subscribing to predetermined standards;
   e) adding the image data in a "ground truth" database for use in further enhancing the iterative algorithm used in the interpretation of the patient images processed through the patient screening centers; and
   f) using the newly updated "ground truth" database to refine the iterative algorithm.

4. The method of detecting medical abnormalities, as defined in claim 1, wherein charges for the service generated by medically interpreting the image is automatically calculated and billed to the originator of the medical image, immediately after performing step c) of claim 1.

* * * * *